(12) United States Patent
Zhu

(10) Patent No.: US 7,479,522 B2
(45) Date of Patent: Jan. 20, 2009

(54) SILICONE ELASTOMER COMPOSITION

(75) Inventor: Aijun Zhu, Garrett, IN (US)

(73) Assignee: Momentive Performance Materials Inc., Albany, NY (US)

( * ) Notice: Subject to any disclaimer, the term of this patent is extended or adjusted under 35 U.S.C. 154(b) by 253 days.

(21) Appl. No.: 11/270,189

(22) Filed: Nov. 9, 2005

(65) Prior Publication Data

US 2007/0106016 A1 May 10, 2007

(51) Int. Cl.
C08L 83/04 (2006.01)
C08G 77/04 (2006.01)
(52) U.S. Cl. .................. 524/588; 524/860; 524/861
(58) Field of Classification Search ............ 524/588; 528/31, 32
See application file for complete search history.

(56) References Cited

U.S. PATENT DOCUMENTS

| | | | |
|---|---|---|---|
| 3,957,713 A | 5/1976 | Jeram et al. | |
| 3,996,195 A * | 12/1976 | Sato et al. | 528/31 |
| 4,024,091 A * | 5/1977 | Lee et al. | 521/86 |
| 4,162,243 A | 7/1979 | Lee et al. | |
| 4,339,564 A | 7/1982 | Okamura | |
| 4,340,709 A | 7/1982 | Jeram et al. | |
| 4,340,710 A * | 7/1982 | Brown, Jr. | 528/15 |
| 4,374,967 A | 2/1983 | Brown et al. | |
| 4,427,801 A | 1/1984 | Sweet | |
| 4,539,357 A * | 9/1985 | Bobear | 524/267 |
| 4,584,355 A | 4/1986 | Blizzard et al. | |
| 4,584,361 A | 4/1986 | Janik et al. | |
| 4,585,830 A | 4/1986 | Sweet | |
| 4,645,815 A | 2/1987 | Lewis | |
| 4,722,968 A | 2/1988 | Shimizu et al. | |
| 4,754,013 A * | 6/1988 | Antonen | 528/15 |
| 4,772,515 A | 9/1988 | Hara et al. | |
| 4,946,878 A | 8/1990 | Jensen et al. | |
| 4,987,169 A | 1/1991 | Kuwata et al. | |
| 5,030,433 A | 7/1991 | Mehrotra | |
| 5,086,147 A | 2/1992 | Ikeno et al. | |
| 5,122,562 A | 6/1992 | Jeram et al. | |
| 5,124,090 A | 6/1992 | Shimizu et al. | |
| 5,153,238 A | 10/1992 | Bilgrien et al. | |
| 5,164,461 A | 11/1992 | Mitchell | |
| 5,204,384 A | 4/1993 | Matsushita et al. | |
| 5,204,437 A | 4/1993 | Ikeno et al. | |
| 5,321,058 A | 6/1994 | Fuchigami et al. | |
| 5,380,812 A | 1/1995 | Lutz et al. | |
| 5,399,651 A | 3/1995 | Gentle et al. | |
| 5,431,853 A | 7/1995 | Tsuda et al. | |
| 5,468,826 A | 11/1995 | Gentle et al. | |
| 5,504,147 A | 4/1996 | Fujiki et al. | |
| 5,506,303 A | 4/1996 | Yoshida et al. | |
| 5,516,823 A | 5/1996 | Gentle et al. | |
| 5,534,609 A | 7/1996 | Lewis et al. | |
| 5,548,006 A | 8/1996 | Hirabayashi et al. | |
| 5,573,803 A | 11/1996 | Omessi | |
| 5,587,151 A | 12/1996 | Richard et al. | |
| 5,591,797 A | 1/1997 | Barthel et al. | |
| 5,616,403 A | 4/1997 | Eckberg et al. | |
| 5,674,966 A * | 10/1997 | McDermott et al. | 528/32 |
| 5,677,411 A | 10/1997 | Ward | |
| 5,753,318 A | 5/1998 | Eckberg et al. | |
| 5,770,298 A | 6/1998 | Nakamura | |
| 5,789,084 A * | 8/1998 | Nakamura et al. | 428/447 |
| 5,834,110 A | 11/1998 | Misawa et al. | |
| 5,846,454 A | 12/1998 | Koczo et al. | |
| 5,859,094 A | 1/1999 | Conway et al. | |
| 5,863,968 A * | 1/1999 | Irish et al. | 523/213 |
| 5,919,526 A | 7/1999 | Eckberg et al. | |
| 5,922,470 A | 7/1999 | Bracken | |
| 5,922,795 A * | 7/1999 | McDermott et al. | 524/285 |
| 5,948,339 A * | 9/1999 | McDermott et al. | 264/328.17 |
| 6,004,679 A | 12/1999 | Mitchell | |
| 6,074,703 A | 6/2000 | Eckberg et al. | |
| 6,101,628 A | 8/2000 | Earl | |
| 6,121,362 A | 9/2000 | Wanek et al. | |
| 6,121,368 A * | 9/2000 | Heying et al. | 524/493 |
| 6,124,407 A * | 9/2000 | Lee et al. | 525/478 |
| 6,169,155 B1 * | 1/2001 | Alvarez et al. | 528/15 |
| 6,201,055 B1 * | 3/2001 | Lutz et al. | 524/493 |
| 6,225,433 B1 * | 5/2001 | Isshiki et al. | 528/15 |
| 6,294,635 B1 | 9/2001 | Achenbach et al. | |
| 6,313,190 B1 | 11/2001 | Bublewitz et al. | |

(Continued)

FOREIGN PATENT DOCUMENTS

| | | |
|---|---|---|
| EP | 0563704 | 3/1993 |
| EP | 0745648 | 5/1996 |
| EP | 0732373 | 9/1996 |
| EP | 0826733 | 3/1998 |
| EP | 0878497 | 5/1998 |
| EP | 0982022 | 8/1999 |

(Continued)

OTHER PUBLICATIONS

Daum, Jeremy et al. "Synthesis and Characterization if Novel, Cyclsiloxanes and their Self-and Co-Condensation with Silanol-Terminated Polysimethtlsiloxane" Polymer Preprints, vol. 45, No. 2, 2002, pp. 539-540.
Database Caplus [Online] Chemical Abstracts Service, Comlumbus, Ohio, US: 1988, Kuzmenko, N.YA et al: Etherification of Trichlorophenlsilane with propyl and butyl alcohols XP002331890 Database accession 1988:75470.

(Continued)

Primary Examiner—Randy Gulakowski
Assistant Examiner—Robert Loewe
(74) Attorney, Agent, or Firm—Dominick G. Vicari

(57) ABSTRACT

High tear strength, low hardness silicone elastomer-forming composition is provided using a unique combination(s) of polyorganosiloxanes and organohydrogenpolysiloxanes, where the polyorganosiloxanes and the organohydrogenpolysiloxanes contain both straight-chain and resinous polyorganosiloxanes.

31 Claims, No Drawings

U.S. PATENT DOCUMENTS

| | | | |
|---|---|---|---|
| 6,365,670 B1 | 4/2002 | Fry | |
| 6,372,860 B1 | 4/2002 | Miyoshi et al. | |
| 6,376,603 B1 | 4/2002 | Kashiwagi | |
| 6,379,806 B1 | 4/2002 | Takamura et al. | |
| 6,413,458 B1 | 7/2002 | Pearce | |
| 6,447,190 B1 | 9/2002 | Kwitek | |
| 6,447,922 B1 | 9/2002 | Stein | |
| 6,448,329 B1 | 9/2002 | Hirschi et al. | |
| 6,465,544 B1 | 10/2002 | Bomal et al. | |
| 6,469,101 B2 | 10/2002 | Nahmias et al. | |
| 6,486,237 B1 | 11/2002 | Howe et al. | |
| 6,509,423 B1 | 1/2003 | Zhu | |
| 6,518,371 B1 | 2/2003 | Fink et al. | |
| 6,531,540 B1 | 3/2003 | O'Brien | |
| 6,558,270 B2 | 5/2003 | Kwitek | |
| 6,562,470 B2 | 5/2003 | Lemen | |
| 6,595,214 B1 | 7/2003 | Hecker et al. | |
| 6,602,964 B2 | 8/2003 | Huang | |
| 6,623,864 B1 | 9/2003 | Sweet et al. | |
| 6,642,184 B1 * | 11/2003 | De Ridder | 507/233 |
| 6,648,535 B2 | 11/2003 | Ferrara, Jr. | |
| 6,659,672 B1 | 12/2003 | Kirita | |
| 6,660,281 B1 | 12/2003 | Nakanishi et al. | |
| 6,750,279 B1 * | 6/2004 | Wang | 524/380 |
| 6,790,451 B2 | 9/2004 | Nakanishi | |
| 6,790,533 B2 | 9/2004 | Reitmeier et al. | |
| 6,822,034 B2 | 11/2004 | Hanke | |
| 6,835,015 B2 | 12/2004 | Pearce | |
| 6,866,435 B2 | 3/2005 | Kamamoto | |
| 6,881,807 B2 | 4/2005 | Terada et al. | |
| 6,890,662 B2 | 5/2005 | Yaginuma et al. | |
| 6,998,427 B2 | 2/2006 | Del Torto et al. | |
| 7,090,923 B2 | 8/2006 | Griswold et al. | |
| 7,119,142 B2 | 10/2006 | Higuchi et al. | |
| 2001/0016609 A1 * | 8/2001 | Meguriya et al. | 521/54 |
| 2002/0082340 A1 * | 6/2002 | Hanke et al. | 524/588 |
| 2002/0150771 A1 | 10/2002 | Lewis et al. | |
| 2002/0156223 A1 | 10/2002 | Boudjourk et al. | |
| 2003/0088042 A1 | 5/2003 | Griswold et al. | |
| 2003/0118530 A1 | 6/2003 | O'Brien et al. | |
| 2003/0181624 A1 * | 9/2003 | Kashiwagi et al. | 528/15 |
| 2003/0194332 A1 * | 10/2003 | Jahn et al. | 417/395 |
| 2004/0122142 A1 * | 6/2004 | Meguriya | 524/268 |
| 2004/0132947 A1 * | 7/2004 | Achenbach et al. | 528/15 |
| 2005/0006794 A1 * | 1/2005 | Kashiwagi et al. | 257/788 |
| 2005/0059776 A1 * | 3/2005 | Cray et al. | 524/861 |
| 2005/0136022 A1 | 6/2005 | Perry | |
| 2006/0115657 A1 | 6/2006 | Griswold | |
| 2006/0150527 A1 | 7/2006 | Ohara et al. | |
| 2007/0106015 A1 | 5/2007 | Zhu et al. | |

FOREIGN PATENT DOCUMENTS

| | | |
|---|---|---|
| EP | 0982023 | 8/1999 |
| EP | 0998911 | 8/1999 |
| EP | 1182231 | 2/2002 |
| EP | 1424364 | 6/2004 |
| EP | 1437382 | 7/2004 |
| EP | 1717274 | 11/2006 |
| GB | 971309 | 9/1964 |
| GB | 2196638 | 5/1988 |
| JP | 60155266 | 8/1985 |
| JP | 61181863 | 8/1986 |
| JP | 5065414 | 3/1993 |
| JP | 5271551 | 10/1993 |
| JP | 05272061 | 10/1993 |
| JP | 6100818 | 4/1994 |
| JP | 06-142411 | 5/1994 |
| JP | 07/328318 | 12/1995 |
| WO | WO 93/19122 | 9/1993 |
| WO | WO98/28376 | 7/1998 |
| WO | WO2004/071765 | 8/2004 |

OTHER PUBLICATIONS

Sprung M.M. et al. The Partial Hydrolysis of methyltrimethoxysilane: Journal of the American Chemical Society, vol. 77, Aug. 5, 1955, pp. 4173-4715.

Okawara, Rokuro et al: Alkylalkoxypolysiloxanes, VI. Lower Members of Cyclic methyl-and ethylethoxypolysiloxanes Bulletin of the Chemical Society of Japan, vol. 31, No. 1, Jan. 1958, pp. 22-25.

Okawara, Rokuro et al: Alkylalkoxypolysiloxanes, VIII. Lower Members of Cyclic methyl-and ethylethoxypolysiloxanes Bulletin of the Chemical Society of Japan, vol. 33, No. 5, May 1960, pp. 659-660.

Andrianov, K.A. et al. "Organic Phosphosilicon Compounds of Stereocyclic Structure" Bulletin of the Academy of Sciences of the USSR, Division of Chemical Sciences, vol. 11, 1969, pp. 659-660.

Kovrigin, V.M. et al. "GLC-Mass Spectrometric Investigation of the mechanism of formation of pervinylocatasilasosquioxane in the polycondensation of trichlorovinylsilane in butyl alcohol" Journal of General Chemistry of the USSR, vol. 59, No. 22, 1989, pp. 332-337.

Crandall J.K. et al. "siloxanes from the hydrolysis of isopropyltrimethoxysilane" Journal of Organometallic Chemistry, vol. 49, No. 1, Mar. 8, 1995, pp. 5-13.

Technical Information, Aerosil Versatile and Effective (Mar. 2003).

Gelest, Reactive Silicones: Forging new polymer links (copyright 2004).

* cited by examiner

SILICONE ELASTOMER COMPOSITION

BACKGROUND OF THE INVENTION

1. Field of the Invention

The invention herein relates to silicone elastomer composition and silicone elastomer formed therefrom.

2. Description of Related Art

Silicone elastomer, a phrase that includes elastomeric organopolysiloxane, can be prepared using a variety of organosiloxane oligomers and polymers, and fillers. The choice of a particular combination of organosiloxane, and filler, and reaction conditions is governed at least in part, by the physical properties desired in the cured elastomer. Particular end-use applications could benefit from a high tear strength, low hardness silicone elastomer.

The formulations employed to prepare elastomeric organopolysiloxane range in viscosity from pourable liquids to non-flowable gums, which can be processed only under the high level of shear, achieved using a two- or three-roll rubber mill. Liquid silicone currently can only attain an intermediate tear value with an undesirably high hardness value.

The prior art discloses elastomeric polyorganosiloxanes exhibiting various combinations of properties desired for particular end-use applications, however elastomer exhibiting certain desirable combinations of properties, have not heretofore been provided for various desired end-use applications.

BRIEF DESCRIPTION OF THE INVENTION

In this brief description it is noted that the present inventors have unexpectedly discovered, in one specific embodiment, a curable high tear strength, low hardness silicone elastomer-forming composition(s). This curable high tear strength, low hardness silicone elastomer-forming composition comprises a unique combination(s) of polyorganosiloxanes and organohydrogenpolysiloxanes, where the polyorganosiloxanes and the organohydrogenpolysiloxanes contain both straight-chain and resinous polyorganosiloxanes.

Thus, in one embodiment there is provided a curable high tear strength, low hardness silicone elastomer-forming composition comprising:

(A) at least two organopolysiloxanes each independently containing at least two silicon-bonded alkenyl groups per molecule, provided said at least two organopolysiloxanes (A) contain at least one substantially straight chain organopolysiloxane and at least one substantially resinous organopolysiloxane;

(B) at least two organohydrogenpolysiloxanes each independently containing at least two silicon-bonded hydrogen atoms per molecule, provided said at least two organohydrogenpolysiloxanes (B) contain at least one substantially straight chain organohydrogenpolysiloxane and at least one substantially resinous organohydrogenpolysiloxane said at least two organohydrogenpolysiloxanes (B) being used in an amount such that the mole ratio of total amount of silicon-bonded hydrogen atoms contained in at least two organohydrogenpolysiloxanes (B) to one silicon-bonded alkenyl group contained in at least two organopolysiloxanes (A) is of from about 1.3 to about 2.2;

(C) filler in an amount of from about 15 to about 45 parts per hundred of polyorganosiloxane (A);

(D) catalyst; and, (E) inhibitor.

DETAILED DESCRIPTION OF THE INVENTION

Applicants have discovered in one embodiment, that improved curable high tear strength, low hardness silicone elastomer-forming composition is obtained by using both straight chain and resinous polyorganosiloxanes as well as both straight chain and resinous organohydrogenpolysiloxanes; combined with a specific filler loading level.

Used herein tear strength is measured by ASTM tear B (as specified in ASTM method D-624-86) method and reported as an average of at least 3 bars, where "high" tear strength is a level of tear strength greater than about 180 pounds per inch (ppi).

As used herein hardness is measured by Shore A hardness according to ASTM D-2240-86, where low hardness is a level of hardness less than about 40.

As used herein the terms polyorganosiloxane and organopolysiloxane are interchangeable one with the other.

As used herein the terms organohydrogenpolysiloxane and polyorganohydrogensiloxane are used interchangeably with the other.

It will be understood herein that all uses of the term centistokes were measured at 25 degrees celsius.

It will be understood herein that all specific, more specific and most specific ranges recited herein comprise all subranges therebetween.

It will be understood herein, unless stated otherwise, that all weight percentages are based upon the total weight of curable high tear strength, low hardness silicone elastomer-forming composition.

In one specific embodiment, at least two organopolysiloxanes (A) can be any known or commercially used organopolysiloxane with the provisos that each of at least two organopolysiloxanes (A) independently contains at least two silicon-bonded alkenyl groups per molecule and that at least two organopolysiloxanes (A) contain at least one substantially straight chain organopolysiloxane and at least one substantially resinous organopolysiloxane.

In yet a further embodiment, the organo groups of at least two organopolysiloxanes (A) can be any organo group commonly associated with such polymers and can generally be selected from the non-limiting examples of alkyl radicals of 1 to about 8 carbon atoms, such as methyl, ethyl, propyl; cycloalkyl radicals such as cyclohexyl, cycloheptyl, cyclooctyl; mononuclear aryl radicals such as phenyl, methylphenyl, ethylphenyl; alkenyl radicals such as vinyl and allyl; and haloalkylradicals such as 3, 3, 3, trifluoropropyl. In a more specific embodiment, the organo groups are alkyl radicals of 1 to 8 carbon atoms, and are most specifically methyl. In yet another more specific embodiment, the organo groups comprise methyl and/or phenyl.

In one specific embodiment herein, at least two organopolysiloxanes (A) comprises the reaction product of linear polyorganosiloxane, branched polyorganosiloxane- and three-dimensional network polyorganosiloxane, provided that each of at least two organopolysiloxanes (A) contains at least two alkenyl groups per molecule.

In one other specific embodiment herein at least two polyorganosiloxanes (A) can further comprise, in addition to at least two polyorganosiloxanes that independently contain at least two silicon-bonded alkenyl groups per molecule and at least one substantially straight chain organopolysiloxane and at least one substantially resinous organopolysiloxane; non-alkenyl containing polyorganosiloxane selected from the group consisting of linear polyorganosiloxane, branched polyorganosiloxane, cyclic organopolysiloxane, three-dimensional network polyorganosiloxane, resinous polyorganosiloxane and combinations thereof where each polyorganosiloxane does not contain any alkenyl groups. In one specific embodiment herein, the amount of polyorganosiloxane that does not contain any alkenyl groups as described above can be present in an amount of specifically less than about 5 weight percent based on the total weight of curable hysteretic silicone gel-forming composition described herein.

In one specific embodiment, linear polyorganosiloxane is defined as substantially straight chain polyorganosiloxane that can be terminated with triorganosiloxyl groups (M units) at molecular chain terminals and can have a molecular backbone chain consisting basically of the repetition of diorganosiloxane units (D units), and where $M=R^1R^2R^3SiO_{1/2}$ and $D=R^4R^5SiO_{1/2}$, where $R^1$, $R^2$, $R^3$, $R^4$, and $R^5$ are independently selected from the group consisting of a monovalent hydrocarbon radical of from one to about sixty carbon atoms; an unsaturated monovalent hydrocarbon radical containing from 2 to 10 carbon atoms; and combinations thereof, provided that at least two polyorganosiloxanes (A) contains at least two alkenyl groups per molecule. In one specific embodiment, substantially straight chain polyorganosiloxane as used herein is a polyorganosiloxane that contains specifically less than about 30 weight percent, more specifically less than about 20 weight percent and most specifically less than about 10 weight percent of T and/or Q units, based on the weight of substantially straight chain polyorganosiloxane, where $T=R^6SiO_{3/2}$ and $Q=SiO_{4/2}$ where $R^6$ is selected from the group consisting of a monovalent hydrocarbon radical of from one to about sixty carbon atoms; an unsaturated monovalent hydrocarbon radical containing from 2 to 10 carbon atoms; and combinations thereof, provided that at least two polyorganosiloxanes (A) contains at least two alkenyl groups per molecule.

In one specific embodiment, a substantially straight chain polyorganosiloxane will be a liquid and a substantially resinous polyorganosiloxane will be a solid; although by no means is it to be construed that there cannot be substantially straight chain polyorganosiloxane that is solid and substantially resinous polyorganosiloxane that is liquid. In yet another embodiment, a substantially straight chain organohydrogenpolysiloxane and a substantially resinous organohydrogenpolysiloxane have the same definitions for straight chain and resinous as was provided above with reference to at least two organopolysiloxanes (A).

In another specific embodiment, branched polyorganosiloxane is defined as linear polyorganosiloxane with the proviso that the linear polyorganosiloxane comprises branched silicone chains which requires the polyorganosiloxane to have some T and/or Q functionality, where T and Q are defined as above for substantially straight chain polyorganosiloxane, but not so much T and/or Q functionality that causes branched polyorganosiloxane to form a three-dimensional network and further; branched polyorganosilxane has to have excess D functionality along with some T and/or Q functionality to form branched silicone chains, where D is defined as above.

In another specific embodiment, cyclic polyorganosiloxane is defined as a cyclic structure containing of from about 3 to about 10 silicon atoms and more specifically of from about 3 to about 6 silicon atoms, more specifically still, cyclic polyorganosiloxane has the formula selected from the group consisting of $D_3$, $D_4$, $D_5$, and $D_6$ where D is defined as above.

In another specific embodiment, three-dimensional network polyorganosiloxane is defined as the reaction product of M, D, T and Q units in any possible combination, where M, D, T and Q have the same definitions provided above, provided that three-dimensional network organopolysiloxane contains at least two silicon-bonded alkenyl groups per molecule and comprises at least one D unit in combination with at least one T and/or Q unit, where T, D and Q are defined as above.

In one specific embodiment, substantially resinous polyorganosiloxane which has the general definition of three-dimensional network polyorganosiloxane (A) provided above and further comprises specifically, no less than about 30 weight percent, more specifically no less than about 40 weight percent, and most specifically no less than about 50 weight percent of T and/or Q units based upon the weight of substantially resinous polyorganosiloxane, where T and Q are defined as described above provided that substantially resinous polyorganosiloxane contains at least two silicon-bonded alkenyl groups per molecule.

In one specific embodiment, each of at least one substantially straight chain organopolysiloxane and at least one substantially resinous organopolysiloxane has a viscosity specifically of from about 10 to about 1,000,000, more specifically of from about 25 to about 500,000 and most specifically, of from about 50 to about 100,000 centipoise at 25 degrees celsius, and has the formula:

where
$M=R^7R^8R^9SiO_{1/2}$;
$M^{vi}=R^{10}R^{11}R^{12}SiO_{1/2}$;
$D=R^{13}R^{14}SiO_{2/2}$;
$D^{vi}=R^{15}R^{16}SiO_{2/2}$;
$T=R^{17}SiO_{3/2}$;
$T^{vi}=R^{18}SiO_{3/2}$; and
$Q=SiO_{2/2}$;

where $R^7$, $R^8$, $R^9$, $R^{13}$, $R^{14}$ and $R^{17}$ are independently monovalent hydrocarbon radicals having from one to sixty carbon atoms; $R^{10}$ is a monovalent unsaturated hydrocarbon radical having from two to ten carbon atoms, and $R^{11}$ and $R^{12}$ are independently monovalent hydrocarbon radicals having from one to sixty carbon atoms; $R^{15}$ is a monovalent unsaturated hydrocarbon radical having from two to ten carbon atoms and $R^{16}$ is a monovalent hydrocarbon radical having from one to sixty carbon atoms; $R^{17}$ is a monovalent unsaturated hydrocarbon radical having from two to ten carbon atoms; the stoichiometric subscripts a, b, c, d, e, f, and g are either zero or positive subject to the following limitations: c is greater than 10; d is from zero to about 20; when d=0, b=2; b is from zero to two, provided that when b=0, d=2; b+d is of from 2 to about 20, when b=1, a=1; a+b≧2; and in substantially straight chain organopolysiloxane if e+f+g>0, then a+b+c+d>e+f+g; and in substantially resinous organopolysiloxane if e+f+g>0, then a+b+c+d<e+f+g; and organopolysiloxane (A) contains at least two silicon-bonded alkenyl groups per molecule.

In one specific embodiment herein, at least two polyorganosiloxanes (A) comprises linear polyorganosiloxane as described above, where said linear polyorganosiloxane is at least one linear polyorganosiloxane selected from Table A below and M, $M^{vi}$, D, and $D^{vi}$ have the same unit definitions as provided above for formula $M_aM^{vi}_bD_cD^{vi}_dT_eT^{vi}_fQ_g$ and D(Ph) has the same definition as D provided that $R^{13}$ and/or $R^{14}$ comprises phenyl. It will be understood herein that percent vinyl is the weight percent of vinyl content based on the total weight of the specific organopolysiloxane.

TABLE A

| Formula | Viscosity (cps) | percent vinyl |
|---|---|---|
| polyorganosiloxane with vinyl on chain | 200 | 0.438 |
| $M^{vi}D_{100}M^{vi}$ | about 200 to about 300 | 0.62 |
| $M^{vi}D_{140}M^{vi}$ | about 500 to about 1000 | 0.34 |
| $MD_{160}M^{vi}$ | about 400 to about 700 | 0.195 |
| $M^{vi}D_{420}M^{vi}$ | 4,000 | 0.18 |
| $M^{vi}D_{800}M^{vi}$ | 40,000 | 0.08 |
| Not available | 35,000 | 0.061 |
| $M^{vi}D_{900}M^{vi}$ | 65,000 | 0.08 |
| $M^{vi}D_{1100}M^{vi}$ | 80,000 | 0.06 |
| $MD_xD^{vi}_xM$; vinyl 0.176% | 10,000 | 0.176 |
| $M^{vi}D_{220}D(Ph)_{18}M^{vi}$ | 3,500 | 0.23 |
| $M^{vi}D_{160}D^{vi}_5M^{vi}$ | 500 | 1.65 |
| $M^{vi}D_{75}D^{vi}_{12}M^{vi}$ | 200 | 5.42 |
| $M^{vi}D_{560}D^{vi}_{36}M^{vi}$ | 4,000 | 2 |

In one specific embodiment herein, at least two polyorganosiloxanes (A) can comprise substantially resinous polyorganosiloxane as described above, where said substantially resinous polyorganosiloxane is at least one resinous polyorganosiloxane selected from Table B below and M, $M^{vi}$, $D^{vi}$ and Q have the same unit definitions as provided above for formula $M_aM^{vi}_bD_cD^{vi}_dT_eT^{vi}_fQ_g$:

TABLE B

| Formula | Viscosity (cps) | Percent vinyl/percent of resin in xylene (if available) |
|---|---|---|
| $M_xD^{vi}_xQ_x$ | about 8 to about 13 | 2.5/60 |
| $M^{vi}_{3x}Q_x$ | about 15 to about 150 | 18.5 |
| $M_xQ_xD^{vi}_x$ | about 8 to about 15 | 2.5 |
| $M_xM^{vi}_xQ_x$ | about 10 to about 30 | 2.4/80 |
| $M_xM^{vi}_xQ_x$ | about 8 to about 15 | 2.4/60 |

In one specific embodiment, it will be understood that the at least two silicon-bonded alkenyl groups per molecule contained in each of at least two polyorganosiloxanes (A) can be located at a terminal location and/or between the terminal locations of the at least two polyorganosiloxanes (A); provided that there are at least two silicon-bonded alkenyl groups contained in each of at least two polyorganosiloxanes (A). In another specific embodiment, an alkenyl group as used herein means a straight or branched chain alkenyl group containing from 2 to about 12 carbon atoms per group and at least one double bond between two carbon atoms per group. In yet a further embodiment, non-limiting examples of alkenyl groups include vinyl, propenyl, butenyl, pentenyl, hexeynl, heptenyl, octenyl, nonenyl, decenyl, undecenyl, dodecenyl and combinations thereof.

In one embodiment, compounds suitable as at least two organopolysiloxanes (A) each independently containing at least two silicon-bonded alkenyl groups per molecule include, the non-limiting examples of vinyl-, propenyl- and butenyl-containing polyorganosiloxanes and combinations thereof.

In one embodiment, at least two silicon-bonded alkenyl groups contain from 1 to about 6 carbon atoms. In another embodiment, the at least two silicon-bonded alkenyl groups are vinyl.

In another specific embodiment herein, the substantially resinous organopolysiloxane contributes a majority of the total amount of silicon-bonded alkenyl groups contained in curable high tear strength, low hardness silicone elastomer-forming composition described herein. In another specific embodiment, substantially resinous organopolysiloxane contains specifically of from about 70 to about 95 weight percent, more specifically of from about 75 to about 90 weight percent and most specifically of from about 80 to about 85 weight percent based on the total weight of silicon-bonded alkenyl groups contained in curable high tear strength, low hardness silicone elastomer forming composition described herein.

In another specific embodiment herein, the substantially straight chain organopolysiloxane contributes a minority of the total amount of silicon-bonded alkenyl groups contained in curable high tear strength, low hardness silicone elastomer-forming composition described herein. In another specific embodiment, substantially straight chain organopolysiloxane contains specifically of from about 5 to about 30 weight percent, more specifically of from about 10 to about 25 weight percent and most specifically of from about 15 to about 20 weight percent of the total weight of silicon-bonded alkenyl groups contained in curable high tear strength, low hardness silicone elastomer forming composition described herein In another more specific embodiment herein, the amount of substantially straight chain organopolysiloxane is specifically of from about 55 to about 85 weight percent, more specifically of from about 60 to about 80 weight percent, and most specifically of from about 65 to about 75 weight percent based on the total weight of curable high tear strength, low hardness silicone elastomer-forming composition.

In yet another more specific embodiment herein, the amount of substantially resinous organopolysiloxane is specifically of from about 0.5 to about 5 weight percent, more specifically of from about 1 to about 3 weight percent, and most specifically of from about 1.5 to about 2.5 weight percent based on the total weight of curable high tear strength, low hardness silicone elastomer-forming composition.

In yet a further embodiment, any combination of substantially straight chain polyorganosiloxane and resinous polyorganosiloxane can be used depending on the desired physical properties of a curable high tear strength, low hardness silicone elastomer produced therefrom, provided that at least two organopolysiloxanes (A) each contain at least two silicon-bonded alkenyl groups per molecule and at least two organopolysiloxanes (A) contain at least one substantially straight chain organopolysiloxane and at least one substantially resinous organopolysiloxane.

In order to cross-link at least two organopolysiloxanes (A) and at least two organohydrogenpolysiloxanes(B) and form a two or three dimensional curable high tear strength, low hardness silicone elastomer-forming composition as described herein, there needs to be at least two silicon bonded hydrogens on each of at least two organohydrogenpolysiloxanes (B) and at least two alkenyl groups on each of at least two organopolysiloxanes (A). It will also be understood that formation of cured high tear strength, low hardness silicone elastomer formed herein comprises a two-dimensional or three dimensional cross linked silicone polymer network that is the curable high tear strength, low hardness silicone elastomer-forming composition described herein.

In one specific embodiment, at least two organohydrogenpolysiloxanes (B) can be any known or commercially used organohydrogenpolysiloxane with the provisos that each of at least two organohydrogenpolysiloxanes (B) independently contains at least two silicon-bonded hydrogen atoms per molecule and that at least two organohydrogenpolysiloxanes (B) contain at least one substantially straight chain organohydrogenpolysiloxane and at least one substantially resinous organohydrogenpolysiloxane. In a further specific embodiment herein each of at least two organohydrogenpolysiloxanes (B) can be substantially free of aliphatic unsaturation.

In one specific embodiment, each of at least one substantially straight chain organohydrogenpolysiloxane and at least one substantially resinous organohydrogenpolysiloxane has a viscosity of specifically from 0.1 to about 2000, more specifically of from about 0.5 to about 1000 and most specifically of from about 1 to about 500 centipoise at 25 degrees celsius.

In another specific embodiment, the organo groups of at least two organohydrogenpolysiloxanes (B) can be any organo group such as those described above for at least two organopolysiloxanes (A). In yet another more specific embodiment, the organo groups of at least two organohydrogenpolysiloxanes (B) comprise a methyl and/or phenyl.

In one specific embodiment herein, at least two organohydrogenpolysiloxanes (B) comprises the reaction product of linear organohydrogenpolysiloxane, branched organohydrogenpolysiloxane, and three-dimensional network organohydrogenpolysiloxane provided that at least two organohydrogenpolysiloxanes (B) contains at least two silicon-bonded hydrogen atoms per molecule.

In one specific embodiment, linear organohydrogenpolysiloxane is defined as substantially straight chain organohydrogenpolysiloxane that can be terminated with M units at molecular chain terminals and having a molecular backbone chain consisting basically of the repetition of D units where $M=R^{19}R^{20}R^{21}SiO_{1/2}$ and $D=R^{22}R^{23}SiO_{1/2}$, where $R^{19}$, $R^{20}$, $R^{21}$, $R^{22}$ and $R^{23}$ are independently selected from the group consisting of a monovalent hydrocarbon radical of from one to about sixty carbon atoms; a hydrogen atom; and combinations thereof, provided that at least two organohydrogenpolysiloxanes (B) contains at least two silicon-bonded hydrogen atoms per molecule. In another specific embodiment herein it will be understood that substantially straight chain organohydrogenpolysiloxane is organohydrogenpolysiloxane that comprises specifically less than about 30 weight percent, more specifically less than about 20 weight percent, and most specifically less than about 10 weight percent of T and/or Q units, based upon the weight of substantially straight chain organohydrogenpolysiloxane, where $T=R^{24}SiO_{3/2}$ and $Q=SiO_{4/2}$, where $R^{24}$ is selected from the group consisting of a monovalent hydrocarbon radical of from one to about sixty carbon atoms; a hydrogen atom; and combinations thereof, provided that at least two organohydrogenpolysiloxanes (B) contains at least two silicon-bonded hydrogen atoms per molecule.

In another specific embodiment, branched organohydrogenpolysiloxane is defined as linear organohydrogenpolysiloxane with the proviso that the linear organohydrogenpolysiloxane comprises branched silicone chains which requires branched organohydrogenpolysiloxane to have some T and/or Q functionality, where T and/or Q is defined as above for linear organohydrogenpolysiloxane, but not sufficient T and/or Q-functionality for branched organohydrogenpolysiloxane to form a three-dimensional network; and furthermore, branched organohydrogenpolysiloxane has to have excess D functionality along with some T and/or Q functionality to form branched silicone chains, where D is defined as above for linear organohydrogenpolysiloxane.

In another specific embodiment, cyclic organohydrogenpolysiloxane is defined as a cyclic structure comprising of from about 3 to about 10 silicon atoms and more specifically of from about 3 to about 6 silicon atoms, more specifically still, cyclic organohydrogenpolysiloxane has the formula selected from the group consisting of $D_3$, $D_4$ $D_5$, and $D_6$ where $D=R^{25}R^{26}SiO_{1/2}$ where $R^{25}$ and $R^{26}$ are independently monovalent hydrocarbon radicals having from one to sixty carbon atoms provided that cyclic organohydrogenpolysiloxane contains at least two silicon-bonded hydrogen atoms per molecule.

In another specific embodiment, three-dimensional network organohydrogenpolysiloxane is defined as the reaction product of M, D, T and Q units in any possible combination, where M, D, T and Q have the same definitions provided above for substantially straight chain organohydrogenpolysiloxane, provided that three-dimensional network organohydrogenpolysiloxane contains at least two silicon-bonded hydrogen atoms per molecule and comprises at least one D unit in combination with at least one T and/or Q unit, where T, D and Q are defined as above for linear organohydrogepolysiloxane (B).

In one specific embodiment, it will be understood herein that at least two organohydrogenpolysiloxanes (B) can comprise substantially resinous organohydrogenpolysiloxane which has the general definition of three-dimensional network organohydrogenpolysiloxane (B) provided above and further comprises specifically, no less than about 30 weight percent, more specifically, no less than about 40 weight percent, and most specifically no less than about 50 weight percent of T and/or Q units, based upon the weight of substantially resinous organohydrogenpolysiloxane, with T and Q units being defined as described above for linear organohydrogenpolysiloxane (B), provided that organohydrogenpolysiloxane (B) contains at least two silicon-bonded hydrogen atoms per molecule.

In one specific embodiment, there is provided curable high tear strength low hardness silicone elastomer-forming composition where each of at least one substantially straight chain organohydrogenpolysiloxane and at least one substantially resinous organohydrogenpolysiloxane has the formula:

where
$M=R^{27}R^{28}R^{29}SiO_{1/2}$;
$M^H=R^{30}R^{31}HSiO_{1/2}$;
$D=R^{32}R^{33}SiO_{2/2}$;
$D^H=R^{34}HSiO_{2/2}$;
$T=R^{35}SiO_{3/2}$;
$T^H=HSiO_{3/2}$; and
$Q=SiO_{4/2}$;

where $R^{27}$,$R^{28}$, $R^{29}$, $R^{32}$, $R^{33}$, and $R^{35}$ are independently monovalent hydrocarbon radicals having from one to sixty carbon atoms and are substantially free of aliphatic unsaturation; $R^{30}$, $R^{31}$, and $R^{34}$ are independently monovalent hydrocarbon radicals having from one to sixty carbon atoms or hydrogen and are substantially free of aliphatic unsaturation the stoichiometric subscripts h, i, j, k, L, m and n being zero or positive subject to the following limitations: j is greater than 0; k is of from zero to about 20, when k=0, i=2; h is of from zero to about 2; subject to the further limitation that i+k is of from 2 to about 60, when i=1, h=1; h+i≧2; and in at least one substantially straight chain organohydrogenpolysiloxane if L+m+n>0 then h+i+j+k>L+m+n; and in at least one substantially resinous organohydrogenpolysiloxane when L+m+n>0, then L+m+n>h+i+j+k and each of at least two organohydrogenpolysiloxanes (B) contains at least two silicon-bonded hydrogen atoms per molecule.

In another specific embodiment, it will be understood that at least two silicon-bonded hydrogen atoms contained in each of at least two organohydrogenpolysiloxanes (B) can be located at a terminal location and/or between the terminal locations of the at least two organohydrogenpolysiloxanes (B); provided that there are at least two silicon-bonded hydrogen atoms in each of at least two organohydrogenpolysiloxanes (B) per molecule.

In one specific embodiment herein, at least two organohydrogenpolysiloxanes (B) can comprise a linear organohydrogenpolysiloxane as described above, where said linear organohydrogenpolysiloxane is at least one linear organohydrogenpolysiloxane selected from Table C below and M, $M^H$, D, and $D^H$ have the same unit definitions as provided above for formula: $M_hM^H_iD_jD^H_kT_LT^H_mQ_n$. It will be understood that weight percent hydride is based on the weight of the specific organohydrogenpolysiloxane.

TABLE C

| Formula | Viscosity (cps) | weight percent hydride |
|---|---|---|
| $M^HD_3M^H$ | 2 | 0.52 |
| $M^HD_6M^H$ | 2 | 0.346 |
| $M^HD_{25}M^H$ | 25 | 0.11 |
| $M^HD_{50}M^H$ | 50 | 0.055 |
| $M^HD_{50}D^H_{50}M^H$ | 50 | 0.86 |
| $M^HD_{100}D^H_{22}M^H$ | 100 | 0.23 |
| $MD^H_4M$ | 1.5 | 0.098 |
| $MD_{20}D^H_{10}M$ | 30 | 0.4 |
| $MD_{20}D^H_{20}M$ | 30 | 0.74 |
| $MD^H_{20}M$ | 25 | 1.65 |

In another specific embodiment herein, at least two organohydrogenpolysiloxanes (B) can comprise a substantially resinous organohydrogenpolysiloxane as described above, where said substantially resinous organohydrogenpolysiloxane is at least one resinous organohydrogenpolysiloxane selected from Table D below and M, $M^H$, T and Q have the same unit definitions as provided above for formula $M_hM^H_iD_jD^H_kT_LT^H_mQ_n$:

TABLE D

| Formula | Viscosity (cps) | weight percent hydride |
|---|---|---|
| $M^H_3M_{12}T_{10}Q_{10}$ | about 40 to about 200 | 700 ppm |
| $M^H_{2x}Q_x$ | about 10 to about 26 | 0.9 |

In yet another specific embodiment, it will be understood that at least two silicon-bonded hydrogen atoms contained in at least two organohydrogenpolysiloxanes (B) can be located at a terminal location and/or between the terminal locations of each at least two organohydrogenpolysiloxanes (B); provided that there are at least two silicon-bonded hydrogen atoms in at least two organohydrogenpolysiloxanes (B) per molecule.

In one embodiment herein at least two organohydrogenpolysiloxanes (B) can comprise two or more of the same or different substantially straight chain organohydrogenpolysiloxanes as described herein. In another specific embodiment herein at least two organohydrogenpolysiloxanes (B) can comprise two or more of the same or different substantially resinous organohydrogenpolysiloxanes as described herein.

In yet a further specific embodiment, any combination of substantially straight chain organohydrogenpolysiloxane and substantially resinous organohydrogenpolysiloxane can be used depending on the desired physical properties of the curable high tear strength, low hardness silicone elastomer produced therefrom, provided that at least two organohydrogenpolysiloxanes (B) each contain at least two silicon-bonded hydrogen atoms per molecule and at least two organohydrogenpolysiloxanes (B) contain at least one substantially straight chain organopolysiloxane and at least one substantially resinous organohydrogenpolysiloxane.

In one other specific embodiment, at least two organopolysiloxanes (A) and at least two organohydrogenpolysiloxanes (B) are used in amounts that will provide desirable curable high tear strength, low hardness silicone composition and/or desirable curable high tear strength, low hardness silicone elastomer.

In one specific embodiment, said at least two organohydrogenpolysiloxanes (B) are used in an amount such that the mole ratio of total amount of silicon-bonded hydrogen atoms contained in at least two organohydrogenpolysiloxanes (B) to one silicon-bonded alkenyl group contained in at least two organopolysiloxanes (A) is specifically of from about 1.3 to about 2.2, more specifically of from about 1.4 to about 2.0 and most specifically of from about 1.5 to about 1.8.

In one specific embodiment, the phrase "total amount of silicon-bonded hydrogen atoms" as used herein refers to the mathematical sum of all of the occurrences of a Si—H bond in all of the individual molecules contained in at least two organohydrogenpolysiloxanes (B).

In another specific embodiment herein, substantially resinous organohydrogenpolysiloxane contributes a majority of the total amount of silicon-bonded hydrogen atoms in the curable high tear strength, low hardness silicone elastomer-forming composition described herein. In another specific embodiment, substantially resinous organohydrogenpolysiloxane contains specifically of from about 65 to about 85 weight percent, more specifically of from about 68 to about 82 weight percent and most specifically of from about 70 to about 80 weight percent based on the total weight of silicon-bonded hydrogen atoms contained in curable high tear strength, low hardness silicone elastomer-forming composition described herein.

In another specific embodiment herein, the substantially straight chain organohydrogenpolysiloxane contributes a minority of the total amount of silicon-bonded hydrogen atoms in the curable high tear strength, low hardness silicone elastomer-forming composition described herein. In another specific embodiment, substantially straight chain organohydrogenpolysiloxane contains specifically of from about 15 to about 35 parts by weight, more specifically of from about 18 to about 32 parts by weight, and most specifically of from about 20 to about 30 parts by weight of the total amount of at least two silicon-bonded hydrogen atoms in the curable high tear strength, low hardness silicone elastomer-forming composition described herein.

In another more specific embodiment herein, the amount of substantially straight chain organohydrogenpolysiloxane is specifically of from about 0.5 to about 5 weight percent, more specifically of from about 0.7 to about 3.5 weight percent, and most specifically of from about 1.0 to about 2.0 weight percent based on the total weight of curable high tear strength, low hardness silicone elastomer-forming composition.

In yet another more specific embodiment herein, the amount of substantially resinous organohydrogenpolysiloxane is specifically of from about 0.5 to about 7 weight percent, more specifically of from about 1 to about 4 weight percent, and most specifically of from about 1.5 to about 2.5 weight percent based on the total weight of curable high tear strength, low hardness silicone elastomer-forming composition.

In one specific embodiment, at least two organopolysiloxanes (A) and at least two organohydrogenpolysiloxanes (B) are used in amounts that will provide desirable curable high tear strength, low hardness silicone elastomer-forming composition and/or desirable high tear strength, low hardness silicone elastomer.

In another specific embodiment, filler (C) can be known or commercially used filler. In yet a further specific embodiment, filler (C) is a component that is usually used in silicone rubber or any other rubbers to import physical and mechanical strength to cured silicone rubber. In one embodiment, filler (C) can be any of the non-limiting examples selected from the group consisting of where filler is selected from the group consisting of silica, fumed silica, precipitated silica, titania, alumina, clay, wollastonite quartz, and combinations thereof. In one specific embodiment, filmed silica, and carbon black are non-limiting examples of reinforcing filler. In another specific embodiment herein, there are provided semi-reinforcing fillers, such as the non-limiting examples of precipitated silica, treated clay and treated wollastonite. In another specific embodiment herein, silica, titania, alumina, clay, and quartz are some non-limiting examples of extending fillers. In one specific embodiment herein, filler (C) comprises reinforcing filler and optionally any other filler described herein. In one specific embodiment herein fumed silica can be commercially available filmed silica.

In one embodiment herein, filler (C) is provided in an amount that imports a desired physical strength while simultaneously controlling hardness.

In one embodiment herein, filler (C) is provided in an amount that imparts a desired physical strength. In one specific embodiment, filler (C) is present in an amount specifically of from 15 to about 30 weight percent, more specifically of from about 18 to about 28 weight percent, and most specifically of from about 20 to about 25 weight percent based on the total weight of curable high tear strength, low hardness silicone elastomer-forming composition.

In one specific embodiment, filler (C) is present in an amount specifically of from about 18 to about 45 parts by weight, more specifically of from about 24 to about 43 parts by weight, and most specifically of from about 28 to about 35 parts by weight per 100 parts of at least two organopolysiloxanes (A).

In one specific embodiment herein there is provided filler (C) that can comprise two or more fillers that are different and further where those fillers can be either treated or untreated.

In one specific embodiment herein, filler can have a surface area specifically of from about 30 microns to about 400 m$^2$/g more specifically of from about 5 microns to about 300 m$^2$/g and most specifically of from about 50 m$^2$/g to about 200 m$^2$/g. In another specific embodiment, filler can have a particle size (average diameter) of about 5 nanometers (nm) to about 200 nanometers, more specifically, of from about 7 nm to about 100 nm and most specifically about 10 nm to about 50 nm.

In yet another specific embodiment, catalyst (D) can be any known or commercially used catalyst that will accelerate the curing caused by the addition reaction of at least two polyorganosiloxanes (A) with at least two organohydrogenpolysiloxanes (B). In one specific embodiment, catalyst (D) is at least one Group VIIIB catalyst. In one other specific embodiment, catalyst (D) is a platinum catalyst. In yet a further embodiment, non-limiting examples of platinum catalysts include platinum black, chloroplatinic acid, alcohol-modified products of chloroplatinic acid, and complexes of chloroplatinic acid with olefins, aldehydes, vinylsiloxanes or acetylene alcohols and combinations thereof. In another specific embodiment, catalyst (D) is a palladium catalyst with non-limiting examples such as tetrakis(triphenylphosphine)palladium. In yet another specific embodiment, catalyst (D) is a rhodium catalyst with non-limiting examples such as rhodium-olefin complexes and chlorotris(triphenylphosphine)rhodium. In one embodiment, catalyst (D) can be added in what is called a catalytically-effective quantity, which can appropriately be made large or small in accordance with the desired curing rate. In one specific embodiment, catalyst (D) can be present specifically in an amount ranging of from about 3 to about 30 parts per million (ppm), more specifically of from about 5 to about 20 ppm, and most specifically of from about 10 to about 15 ppm. In one embodiment the amount of catalyst (d) is the total amount of platinum metal present in high tear strength, low hardness silicone elastomer-forming composition described herein.

In one specific embodiment herein there is provided catalyst (D) that can comprise two or more catalysts that are different.

In yet still another specific embodiment, inhibitor (E) can be any known or commercially used inhibitor that will adequately control curing time of components (A), (B), (C) and (D) and allow the curable hysteretic silicone gel-forming composition to be put to practical use. In one specific embodiment inhibitor (E) can contain aliphatic unsaturation. In another specific embodiment, inhibitor (E) can have no aliphatic unsaturation. In yet a further embodiment, non-limiting examples of inhibitor (E) are selected from the group consisting of diallyl maleate, D-4 vinyl, 2-methyl-3-butene-2-ol, 1-ethynyl-1-cyclohexanol, 3,5,-dimethyl-1-hexyn-3-ol and combinations thereof. In one specific embodiment, inhibitor (E) is used in an amount specifically of from about 0.01 to about 0.2 parts by weight, more specifically of from about 0.015 to about 0.15 parts by weight, and most specifically of from about 0.02 to about 0.06 parts by weight based on the total weight of the curable high tear strength, low hardness silicone elastomer-forming composition.

In one specific embodiment herein there is provided inhibitor (E) that can comprise two or more inhibitors that are different.

In one specific embodiment herein, there is provided curable high tear strength, low hardness silicone elastomer-forming composition comprising the specific formulation where at least two organopolysiloxanes (A) is a combination of (A-i) substantially straight chain vinyl organopolysiloxane having a viscosity of from about 50,000 to about 80,000 centipoise at 25 degrees celsius, and being present in an amount of from about 45 to about 50 weight percent; (A-ii) substantially straight chain vinyl organopolysiloxane having a viscosity of from about 20,000 to about 45,000 centipoise at 25 degrees celsius, and being present in an amount of from about 20 to about 25 weight percent; (; (A-iii) substantially resinous vinyl organopolysiloxane having a viscosity of from about 15 to about 250 centipoise at 25 degrees celsius, and being present in an amount of from about 1.5 to about 2.5 weight percent; at least two organohydrogenpolysiloxanes (B) is a combination of (B-i) substantially straight chain organohydrogenpolysiloxane where (B-i) has terminal group silicon-bonded hydrogen atom and additional silicon-bonded hydrogen atom beyond terminal group silicon-bonded hydrogen atom per molecule and having a viscosity of from about 15 to about 100 centipoise at 25 degrees celsius, being present in an amount of from about 0.5 to about 1 weight percent; and (B-ii) substantially straight chain organohydrogenpolysiloxane containing silicon-bonded hydrogen atoms that are only terminal group silicon-bonded hydrogen atoms per molecule and having a viscosity of from 1 to about 10 centipoise at 25 degrees celsius, being present in an amount of from about 0.5 to about 1 weight percent; and (B-iii) substantially resinous organohydrogenpolysiloxane having a viscosity of from about 15 to about 60 centipoise at 25 degrees celsius, and being present in an amount of from about 1.5 to about 2.5 weight percent; filler (C) being fumed silica with a surface area of from about 200 to about 350 m²/g, said fumed silica having been treated with silane, where filler (C) is present in an amount of from about 20 to about 25 weight percent; catalyst (D) is a platinum catalyst where catalyst (D) is present in an amount of from about 5 ppm to about 30 ppm and, inhibitor (E) is 1-ethynyl-1-cyclohexanol where inhibitor (E) is present in an amount of from about 0.02 to about 0.06 weight percent, with all weight percents being based upon the total weight of the curable high tear strength, low hardness silicone elastomer-forming composition.

In one embodiment herein, curable high tear strength, low hardness silicone elastomer-forming composition can be made in conventionally known methods. In one specific method curable high tear strength, low hardness silicone elastomer-forming composition components (A)-(E) can be mixed together in one reaction vessel and subsequently cured with heat and pressure. In one alternative embodiment, curable high tear strength, low hardness silicone elastomer-forming composition components (A)-(E) can be provided in a conventional two mixture system and subsequently cured with heat and pressure.

In another specific embodiment, there is provided herein a high tear strength, low hardness silicone elastomer obtained from the polymerization of the curable high tear strength, low hardness silicone elastomer-forming composition described herein. In yet another specific embodiment, the high tear strength, low hardness silicone elastomer is a liquid injection moldable silicone elastomer.

In one specific embodiment, it will be understood herein that the curing (or crosslinking) of the curable high tear strength, low hardness silicone elastomer-forming composition can be conducted through a method selected from the group consisting of addition curing, condensation curing, and combinations thereof.

In one specific embodiment herein, high tear strength, low hardness silicone elastomer specifically has a tear B value of at least about 180 ppi and a Shore A hardness of less than about 40, more specifically a tear B value of at least 200 ppi and a Shore A hardness of less than about 35, and most specifically has a tear B value of at least about 220 ppi and a Shore A hardness of less than about 33.

In one specific embodiment herein, high tear strength, low hardness silicone elastomer can advantageously be used in various applications that require a high tear strength, low hardness elastomer. In one specific embodiment, some non-limiting examples of such applications are selected from the group consisting of sleep apnea masks, needle-less intravenous applications, peristaltic pump membranes, shoe insoles and catheter balloons.

The examples below are given for the purpose of illustrating the invention of the instant case. They are not being given for any purpose of setting limitations on the embodiments described herein.

EXAMPLES

The example below was made by combining all of the components (A)-(E) in one reaction vessel and subsequently curing them under heat and pressure.

For the subject example:
$M=R^A R^B R^C SiO_{1/2}$;
$M^H=R^F R^G HSiO_{1/2}$;
$M^{vi}=R^J R^K R^L SiO_{1/2}$;
$D=R^M R^N SiO_{2/2}$
$D^H=R^O HSiO_{2/2}$;
$D^{vi}=R^P R^Q SiO_{2/2}$;
$D(Ph)=R^S R^U SiO_{2/2}$ $T=R^V SiO_{3/2}$
$T^H=HSiO_{3/2}$;
$T^{vi}=R^W SiO_{3/2}$ and
$Q=SiO_{2/2}$;

where $R^A$, $R^B$, $R^C$, $R^M$, $R^N$ and $R^V$ are independently monovalent hydrocarbon radicals having from one to sixty carbon atoms; $R^F$, $R^G$, and $R^O$ are independently monovalent hydrocarbon radicals having from one to sixty carbon atoms or hydrogen and are substantially free of aliphatic unsaturation; $R^J$ is a monovalent unsaturated hydrocarbon radical having from two to ten carbon atoms, and $R^K$ and $R^L$ are independently monovalent hydrocarbon radicals having from one to sixty carbon atoms; $R^P$ is a monovalent unsaturated hydrocarbon radical having from two to ten carbon atoms and $R^L$ is a monovalent hydrocarbon radical having from one to sixty carbon atoms; and $R^W$ is a monovalent unsaturated hydrocarbon radical having from two to ten carbon atoms.

The results of one specific formulation are listed here. For this formulation:

At least two organopolysiloxanes (A) consists of a vinyl polymer with a viscosity of 65,000 centipoise at 25 degrees Celsius as described in Table A above, another vinyl polymer with a viscosity of 35,000 centipoise at 25 degrees celsius as described in Table A above, and as well as a vinyl resin with a viscosity around 80 centipoise at 25 degrees Celsius and 18.5 weight percent vinyl content as described in Table B above for resin having a viscosity of from 15 to about 150 centipoise.

At least two organohydrogenpolysiloxanes (B) includes a linear hydride with multiple Si—H groups on the chain with a viscosity of 30 centipoise with a hydride content of 0.4 as described in Table C above another linear hydride which is Si—H terminated only with a viscosity of 2 centipoise at 25 degrees celsius and a hydride content of 0.346 as described in Table C above and a hydride resin with a viscosity of 18 centipoise with a hydride content of 0.9 as described in Table D.

Filler C is commercially available fumed silica with about a 300 m²/g specific surface area, which has been in-situ treated with hexamethyldisilazane (HMDZ) in production.

Catalyst (D) is a high concentration of Karstead's catalyst and inhibitor (E) is 1-ethynyl-1-cyclohexanol (ECH).

It will be understood herein that parts by weight can be converted into weight percentage based on the total weight of curable hysteretic silicone gel-forming composition described herein by taking each component described herein and taking the ratio of sum total of the parts by weight of that component and dividing it by the sum of the total parts by weight of all of the components and multiplying this ratio by 100 to get the weight percentage of that component.

Standard ASTM sheets are molded at 176.6 degrees celsius. Tear strength was tested according to ASTM Tear B method, and data was reported as an average of at least 3 tear bars. Hardness was reported as Shore A hardness.

All batches had excellent physical properties similar to conventional elastomer, with tensile strength of about 1,000 psi, and elongation of about 750 percent.

Typical tear B and Hardness values of LIM6030, a standard under 40 Duro GE liquid silicone rubber, is included for comparison.

TABLE 1

| Material | Tear Strength (ppi) | Hardness (Shore A) |
|---|---|---|
| Batch 1 | 235 | 33 |
| Batch 2 | 250 | 34 |
| Batch 3 | 235 | 31 |
| LIM6030 | 150 | 34 |

The above described batches in Table 1 are materials made at different times by different equipment, but with the same formulation. This is done to test the robustness of the formulation. The formulation described herein in the examples was the formulation that had the best high tear property.

The subject example utilized a ratio of (B) to (A) of 1.58

As described above, this formulation is able to produce silicone rubbers with much higher tear strength (greater than 200 ppi) than current commercial grade silicone elastomer at a hardness lower than 35 Shore A. The concept of combining different types of vinyl and hydride silicone fluids has proved to be useful for improving the tear strength of silicone elastomer without sacrificing the softness of the material.

In the subject example, the following components as described in Table 2 were used:

TABLE 2

| Components (A)-(E) | Weight Percent | Viscosity in centipoises at 25 degrees celsius | Formula | Note |
|---|---|---|---|---|
| (A): | 49.11 | 65,000 | $M^{Vi}D_{900}M^{Vi}$; | vinyl |
| (A): | 22.71 | 35,000 | $M^{Vi}D_{690}M^{Vi}$ | vinyl |
| (A): | 1.80 | 15 to about 150 | $M^{Vi}_3Q$ | Vinyl Resin |
| (B): | 0.73 | 30 | $MD_{20}D^H_{10}M$ | H on chain |
| (B): | 1.80 | 20 | $M^H_2Q$; 20 cPs; Wt. % H 0.90 | Hydride Resin |
| (B): | 0.70 | about 5 | $M^H D_6 M^H$ | H stopped |
| (C): Treated Silica | 23.10 | | | filler |
| (D): Pt-s | 0.0039 | | | Platinum catalyst |
| (E): ECH | 0.03 | | | 1-ethynyl-1-cyclohexanol |

While the above description comprises many specifics, these specifics should not be construed as limitations, but merely as exemplifications of specific embodiments thereof. Those skilled in the art will envision many other embodiments within the scope and spirit of the description as defined by the claims appended hereto.

The invention claimed is:

1. A curable high tear strength, low hardness silicone elastomer-forming composition comprising:

(A) at least two organopolysiloxanes each independently containing at least two silicon-bonded alkenyl groups per molecule, provided said at least two organopolysiloxanes (A) contain at least one substantially straight chain organopolysiloxane and at least one substantially resinous organopolysiloxane;

(B) at least two organohydrogenpolysiloxanes each independently containing at least two silicon-bonded hydrogen atoms per molecule, provided said at least two organohydrogenpolysiloxanes (B) contain at least one substantially straight chain organohydrogenpolysiloxane and at least one substantially resinous organohydrogenpolysiloxane said at least two organohydrogenpolysiloxanes (B) being used in an amount such that the mole ratio of total amount of silicon-bonded hydrogen atoms contained in at least two organohydrogenpolysiloxanes (B) to silicon-bonded alkenyl groups contained in at least two organopolysiloxanes (A) is of from about 1.3 to about 2.2;

(C) filler in an amount of from about 15 to about 45 parts per hundred of polyorganosiloxane (A);

(D) catalyst; and, (E) inhibitor, and where combined (A)-(E) comprises a curable high tear strength, low hardness silicone elastomer-forming composition, wherein when said composition is cured it has a Shore A hardness of less than about 35.

2. The curable high tear strength, low hardness silicone elastomer forming composition of claim 1 where at least two organopolysiloxanes (A) comprises the reaction product of linear polyorganosiloxane and branched polyorganosiloxane.

3. The curable high tear strength, low hardness silicone elastomer forming composition of claim 1 where at least two polyorganosiloxanes (A) can further comprise, in addition to at least two polyorganosiloxanes that independently contain at least two silicon-bonded alkenyl groups per molecule and at least one substantially straight chain organopolysiloxane and at least one substantially resinous organopolysiloxane; non-alkenyl containing polyorganosiloxane selected from the group consisting of linear polyorganosiloxane, branched polyorganosiloxane, cyclic organopolysiloxane, three-dimensional network polyorganosiloxane, resinous polyorganosiloxane and combinations thereof where each polyorganosiloxane does not contain any alkenyl groups.

4. The curable high tear strength, low hardness silicone elastomer forming composition of claim 1 where substantially straight chain polyorganosiloxane is polyorganosiloxane that comprises less than about 30 weight percent of T and/or Q units where $T=R^6SiO_{3/2}$ and $Q=SiO_{4/2}$ where $R^6$ is selected from the group consisting of a monovalent hydrocarbon radical of from one to about sixty carbon atoms; an unsaturated monovalent hydrocarbon radical containing from 2 to 10 carbon atoms; and combinations thereof.

5. The curable high tear strength, low hardness silicone elastomer forming composition of claim 1 where substantially resinous polyorganosiloxane is polyorganosiloxane that comprises no less than about 30 weight percent, of T and/or Q units where $T=R^6SiO_{3/2}$ and $Q=SiO_{4/2}$ where $R^6$ is selected from the group consisting of a monovalent hydrocarbon radical of from one to about sixty carbon atoms; an unsaturated monovalent hydrocarbon radical containing from 2 to 10 carbon atoms; and combinations thereof.

6. The curable high tear strength, low hardness silicone elastomer-forming composition of claim 1 where each of substantially straight chain organopolysiloxane and substantially resinous organopolysiloxane has a viscosity of from about 10 to about 1,000,000 centipoise at 25 degrees celsius and has the formula:

$$M_a M^{vi}_b D_c D^{vi}_d T_e T^{vi}_f Q_g$$

where
M=$R^7R^8R^9SiO_{1/2}$;
$M^{vi}$=$R^{10}R^{11}R^{12}SiO_{1/2}$;
D=$R^{13}R^{14}SiO_{2/2}$;
$D^{vi}$=$R^{15}R^{16}SiO_{2/2}$;
T=$R^{17}SiO_{3/2}$;
$T^{vi}$=$R^{18}SiO_{3/2}$; and
Q=$SiO_{2/2}$;
where $R^7$, $R^8$, $R^9$, $R^{13}$, $R^{14}$ and $R^{17}$ are independently monovalent hydrocarbon radicals having from one to sixty carbon atoms; $R^{10}$ is a monovalent unsaturated hydrocarbon radical having from two to ten carbon atoms, and $R^{11}$ and $R^{12}$ are independently monovalent hydrocarbon radicals having from one to sixty carbon atoms; $R^{15}$ is a monovalent unsaturated hydrocarbon radical having from two to ten carbon atoms and $R^{16}$ is a monovalent hydrocarbon radical having from one to sixty carbon atoms; $R^{17}$ is a monovalent unsaturated hydrocarbon radical having from two to ten carbon atoms; the stoichiometric subscripts a, b, c, d, e, f, and g are either zero or positive subject to the following limitations: c is greater than 10; d is from zero to about 20; when d=0, b=2; b is from zero to two, provided that when b=0, d=2; b+d is of from 2 to about 20, when b=1, a=1; a+b≧2; and in substantially straight chain organopolysiloxane if e+f+g>0, then a+b+c+d>e+f+g; and in substantially resinous organopolysiloxane if e+f+g>0, then a+b+c+d<e+f+g; and organopolysiloxane (A) contains at least two silicon-bonded alkenyl groups per molecule.

7. The curable high tear strength, low hardness silicone elastomer-forming composition of claim 1 where at least two silicon-bonded alkenyl groups contain from 2 to about 6 carbon atoms.

8. The curable high tear strength, low hardness silicone elastomer-forming composition of claim 1 where at least two silicon-bonded alkenyl groups are vinyl.

9. The curable high tear strength, low hardness silicone elastomer-forming composition of claim 1 where organo groups of at least two polyorganosiloxanes (A) comprise methyl and/or phenyl.

10. The curable high tear strength, low hardness silicone elastomer-forming composition of claim 1 where at least two organohydrogenpolysiloxanes (B) comprises the reaction product of linear organohydrogenpolysiloxane, branched organohydrogenpolysiloxane and cyclic organohydrogenpolysiloxane.

11. The curable high tear strength, low hardness silicone elastomer forming composition of claim 1 where substantially straight chain organohydrogenpolysiloxane is organohydrogenpolysiloxane that comprises less than about 30 weight percent of T and/or Q units where T=$R^{24}SiO_{3/2}$ and Q=$SiO_{4/2}$, where $R^{24}$ is selected from the group consisting of a monovalent hydrocarbon radical of from one to about sixty carbon atoms; an unsaturated monovalent hydrocarbon radical containing from 2 to 10 carbon atoms; and combinations thereof.

12. The curable high tear strength, low hardness silicone elastomer forming composition of claim 1 where substantially resinous organohydrogenpolysilxoane is organohydrogenpolysiloxane that comprises no less than about 30 weight percent, of T and/or Q units where T=$R^{24}SiO_{3/2}$ and Q=$SiO_{4/2}$, where $R^{24}$ is selected from the group consisting of a monovalent hydrocarbon radical of from one to about sixty carbon atoms; an unsaturated monovalent hydrocarbon radical containing from 2 to 10 carbon atoms; and combinations thereof.

13. The curable high tear strength, low hardness silicone elastomer-forming composition of claim 1 where each substantially straight chain organohydrogenpolysiloxane and each substantially resinous organohydrogenpolysiloxane has the formula:

$$M_h M^H_i D_j D^H_k T_L T^H_m Q_n$$

where
M=$R^{27}R^{28}R^{29}SiO_{1/2}$;
$M^H$=$R^{30}R^{31}HSiO_{1/2}$;
D=$R^{32}R^{33}SiO_{2/2}$;
$D^H$=$R^{34}HSiO_{2/2}$;
T=$R^{35}SiO_{3/2}$;
$T^H$=$HSiO_{3/2}$; and
Q=$SiO_{4/2}$;
where $R^{27}$, $R^{28}$, $R^{29}$, $R^{32}$, $R^{33}$, and $R^{35}$ are independently monovalent hydrocarbon radicals having from one to sixty carbon atoms and are substantially free of aliphatic unsaturation; $R^{30}$, $R^{31}$, and are independently monovalent hydrocarbon radicals having from one to sixty carbon atoms or hydrogen and are substantially free of aliphatic unsaturation the stoichiometric subscripts h, i, j, k, L, m and n being zero or positive subject to the following limitations: j is greater than 0; k is of from zero to about 20, when k=0, i=2; h is of from zero to about 2; subject to the further limitation that i+k is of from 2 to about 60, when i=1, h=1; h+i≧2; and in at least one substantially straight chain organohydrogenpolysiloxane if L+m+n>0 then h+i+j+k>L+m+n; and in at least one substantially resinous organohydrogenpolysiloxane when L+m+n>0, then L+m+n>h+i+j+k and each of at least two organohydrogenpolysiloxanes (B) contains at least two silicon-bonded hydrogen atoms per molecule.

14. The curable high tear strength, low hardness silicone elastomer-forming composition of claim 13 wherein i+k is of from 2 to about 20.

15. The curable high tear strength, low hardness silicone elastomer-forming composition of claim 1 where each substantially straight chain organohydrogenpolysiloxane and each substantially resinous organohydrogenpolysiloxane has a viscosity of from about 0.1 to about 2000 centipoise at 25 degrees Celsius.

16. The curable high tear strength, low hardness silicone elastomer-forming composition of claim 1 where each of at least one substantially straight chain organohydrogenpolysiloxane and at least one substantially resinous organohydrogenpolysiloxane has a viscosity of from about 0.5 to about 1000 centipoise at 25 degrees celsius.

17. The curable high tear strength, low hardness silicone elastomer-forming composition of claim 1 where each of at least one substantially straight chain organohydrogenpolysiloxane and at least one substantially resinous organohydrogenpolysiloxane has a viscosity of from 1 to about 500 centipoise at 25 degrees celsius.

18. The curable high tear strength, low hardness silicone elastomer-forming composition of claim 1 where the mole ratio of the total amount of silicon-bonded hydrogen atoms contained in at least two organohydrogenpolysiloxanes (B) to the total amount of silicon-bonded alkenyl groups contained in at least two organopolysiloxanes (A) is of from about 1.4 to about 2.0.

19. The curable high tear strength, low hardness silicone elastomer-forming composition of claim 1 where the mole ratio of the total amount silicon-bonded hydrogen atoms contained in at least two organohydrogenpolysiloxanes (B) to the total amount of silicon-bonded alkenyl groups contained in at least two organopolysiloxanes (A) is of from about 1.5 to about 1.8.

20. The curable high tear strength, low hardness silicone elastomer-forming composition of claim 1 where filler (C) is present in an amount of from about 20 to about 40 parts by weight per 100 parts of at least two organopolysiloxanes (A).

21. The curable high tear strength, low hardness silicone elastomer-forming composition of claim 1 where filler (C) is present in an amount of from about 25 to about 35 parts by weight per 100 parts of at least two organopolysiloxanes (A).

22. The curable high tear strength, low hardness silicone elastomer-forming composition of claim 1 where filler is selected from the group consisting of silica, fumed silica, precipitated silica, titania, alumina, clay, wollastonite quartz, and combinations thereof.

23. The curable high tear strength, low hardness silicone elastomer-forming composition of claim 1 where catalyst (D) is at least one Group VIIIB catalyst.

24. The curable high tear strength, low hardness silicone elastomer-forming composition of claim 1 where inhibitor (E) contains aliphatic unsaturation and is selected from the group consisting of diallyl maleate, D-4 vinyl, 2-methyl-3-butene-2-ol, 1-ethynyl-1-cyclohexanol, 3,5,-dimethyl- 1-hexyn-3-ol and combinations thereof.

25. The high tear strength, low hardness silicone elastomer obtained from the curing of the curable high tear strength, low hardness silicone elastomer-forming composition of claim 1.

26. The high tear strength, low hardness silicone elastomer of claim 25 where the high tear strength, low hardness silicone elastomer is liquid injection moldable silicone elastomer.

27. The liquid injection moldable silicone elastomer of claim 26 where the elastomer has a tear B value of at least about 220 ppi and a Shore A hardness of less than about 33.

28. The high tear strength, low hardness silicone elastomer of claim 25 where the elastomer has a tear B value of at least about 180 ppi and a Shore A hardness of less than about 35.

29. The high tear strength, low hardness silicone elastomer of claim 25 where the elastomer has a tear B value of at least about 200 ppi and a Shore A hardness of less than about 35.

30. The high tear strength, low hardness silicone elastomer of claim 25 where the elastomer is used in an application selected from the group consisting of sleep apnea masks, needle-less intravenous applications, peristaltic pump membranes, shoe insoles and catheter balloons.

31. A curable high tear strength, low hardness silicone elastomer-forming composition comprising:
(A) at least two organopolysiloxanes each independently containing at least two silicon-bonded alkenyl groups per molecule, wherein at least two organopolysiloxanes (A) is a combination of (A-i) substantially straight chain vinyl organopolysiloxane having a viscosity of from about 50,000 to about 80,000 centipoise at 25 degrees celsius, and being present in an amount of from about 45 to about 50 weight percent; (A-ii) substantially straight chain vinyl organopolysiloxane having a viscosity of from about 20,000 to about 45,000 centipoise at 25 degrees celsius, and being present in an amount of from about 20 to about 25 weight percent; (A-iii) substantially resinous vinyl organopolysiloxane having a viscosity of from about 15 to about 250 centipoise at 25 degrees celsius, and being present in an amount of from about 1.5 to about 2.5 weight percent;
(B) at least two organohydrogenpolysiloxanes each independently containing at least two silicon-bonded hydrogen atoms per molecule, wherein at least two organohydrogenpolysiloxanes (B) is a combination of (B-i) substantially straight chain organohydrogenpolysiloxane where (B-i) has terminal group silicon-bonded hydrogen atom and additional silicon-bonded hydrogen atom beyond terminal group silicon-bonded hydrogen atom per molecule and having a viscosity of from about 15 to about 100 centipoise at 25 degrees celsius, being present in an amount of from about 0.5 to about 1 weight percent; and (B-ii) is substantially straight chain organohydrogenpolysiloxane containing silicon-bonded hydrogen atoms that are only terminal group silicon-bonded hydrogen atoms per molecule and having a viscosity of from 1 to about 10 centipoise at 25 degrees celsius, being present in an amount of from about 0.5 to about 1 weight percent; and (B-iii) substantially resinous organohydrogenpolysiloxane having a viscosity of from about 15 to about 60 centipoise at 25 degrees celsius, and being present in an amount of from about 1.5 to about 2.5 weight percent;
said at least two organohydrogenpolysiloxanes (B) being used in an amount such that the mole ratio of total amount of silicon-bonded hydrogen atoms contained in at least two organohydrogenpolysiloxanes (B) to silicon-bonded alkenyl groups contained in at least two organopolysiloxanes (A) is of from about 1.3 to about 2.2;
(C) filler in an amount of from about 15 to about 45 parts per hundred of polyorganosiloxane (A), wherein said filler (C) is finned silica with a surface area of from about 200 to about 350 $m^2/g$, said fumed silica having been treated with silane, and where filler (C) is present in an amount of from about 20 to about 25 weight percent;
(D) a platinum catalyst which is present in an amount of from about 5 ppm to about 30 ppm; and,
(E) 1-ethynyl- 1-cyclohexanol where said 1-ethynyl- 1-cyclohexanol is present in an amount of from about 0.02 to about 0.06 weight percent, with all weight percents being based upon the total weight of the curable high tear strength, low hardness silicone elastomer-forming composition, and where combined (A)-(E) comprises a curable high tear strength, low hardness silicone elastomer-forming composition.

* * * * *